(12) United States Patent
Keibel

(10) Patent No.: US 11,660,159 B2
(45) Date of Patent: May 30, 2023

(54) INSTRUMENT TRAY FOR SURGICAL INSTRUMENTS

(71) Applicant: KUKA Deutschland GmbH, Augsburg (DE)

(72) Inventor: Andreas Keibel, Augsburg (DE)

(73) Assignee: KUKA Deutschland GmbH, Augsburg (DE)

( * ) Notice: Subject to any disclaimer, the term of this patent is extended or adjusted under 35 U.S.C. 154(b) by 682 days.

(21) Appl. No.: 16/622,496

(22) PCT Filed: May 30, 2018

(86) PCT No.: PCT/EP2018/064128
§ 371 (c)(1),
(2) Date: Dec. 13, 2019

(87) PCT Pub. No.: WO2018/228818
PCT Pub. Date: Dec. 20, 2018

(65) Prior Publication Data
US 2020/0205926 A1  Jul. 2, 2020

(30) Foreign Application Priority Data

Jun. 13, 2017 (DE) ..................... 10 2017 209 966.6

(51) Int. Cl.
*B65D 83/10* (2006.01)
*A61B 50/33* (2016.01)
(Continued)

(52) U.S. Cl.
CPC .............. *A61B 50/33* (2016.02); *A61B 50/13* (2016.02); *A61B 50/34* (2016.02); *A61B 90/90* (2016.02);
(Continued)

(58) Field of Classification Search
CPC ......... A61B 50/13; A61B 50/33; A61B 90/90; A61L 2/07; A61L 2/24; A61L 2202/182;
(Continued)

(56) References Cited

U.S. PATENT DOCUMENTS 5,681,539 A * 10/1997 Riley ..................... A61B 50/22
206/370
5,827,487 A * 10/1998 Holmes ..................... A61L 2/26
206/483

(Continued)

FOREIGN PATENT DOCUMENTS

DE  102004053355 A1  5/2006
DE  102007003222 A1  7/2008
DE  102010021037 A1  11/2011

OTHER PUBLICATIONS

European Patent Office; Office Action in related European Patent Application No. 18 728 357.7 dated May 23, 2022; 5 pages.
(Continued)

*Primary Examiner* — Luan K Bui
(74) *Attorney, Agent, or Firm* — Dorton & Willis, LLP

(57) ABSTRACT

An instrument tray for storing and supplying surgical instruments, and a system and a method for at least semi-automatically handling trays of this type. The tray includes a container for receiving surgical instruments, and the container has unique visual markers for individual instruments. The system also includes a manipulator and an image recognition unit.

4 Claims, 2 Drawing Sheets

(51) Int. Cl.
  *A61B 50/13* (2016.01)
  *A61B 50/34* (2016.01)
  *A61B 90/90* (2016.01)
  *A61L 2/07* (2006.01)
  *A61L 2/24* (2006.01)
  *B25J 9/16* (2006.01)
  *B65D 25/10* (2006.01)
  *B65G 61/00* (2006.01)

(52) U.S. Cl.
  CPC .............. *A61L 2/07* (2013.01); *A61L 2/24* (2013.01); *B25J 9/1697* (2013.01); *B65D 25/10* (2013.01); *B65G 61/00* (2013.01); *A61L 2202/182* (2013.01); *A61L 2202/24* (2013.01)

(58) Field of Classification Search
  CPC .... A61L 2202/24; B65D 25/10; B25J 9/1697; B65G 61/00
  USPC .......... 206/363–372, 459.1, 459.5, 438, 565
  See application file for complete search history.

(56) References Cited

U.S. PATENT DOCUMENTS

| | | | | |
|---|---|---|---|---|
| 7,861,860 | B2* | 1/2011 | Bettenhausen | A61L 2/26 206/439 |
| 8,118,162 | B1* | 2/2012 | McEwin | B25H 3/04 206/338 |
| 8,272,508 | B2* | 9/2012 | Bettenhausen | A61L 2/26 206/370 |
| 2007/0009408 | A1* | 1/2007 | Riley | A61L 2/26 422/300 |
| 2007/0205123 | A1* | 9/2007 | Bettenhausen | A61B 50/34 206/370 |
| 2009/0146032 | A1 | 6/2009 | Bettenhausen et al. | |
| 2010/0176016 | A1* | 7/2010 | Pell | A61B 50/33 206/370 |
| 2011/0005342 | A1 | 1/2011 | Treat et al. | |
| 2011/0262250 | A1 | 10/2011 | Treat et al. | |
| 2014/0069841 | A1 | 3/2014 | Pizzato et al. | |
| 2014/0083886 | A1 | 3/2014 | Winterrowd | |
| 2016/0100891 | A1* | 4/2016 | Richman | A61B 50/30 206/370 |

OTHER PUBLICATIONS

European Patent Office; Search Report in related International Patent Application No. PCT/EP2018/064128 dated Aug. 27, 2018; 3 pages.

European Patent Office; Written Opinion in related International Patent Application No. PCT/EP2018/064128 dated Aug. 27, 2018; 8 pages.

German Patent Office; Examination Report in related German Patent Application No. 10 2017 209 966.6 dated Mar. 20, 2018; 7 pages.

European Patent Office; Office Action in related European Patent Application No. 18728357.7 dated Apr. 19, 2021; 5 pages.

* cited by examiner

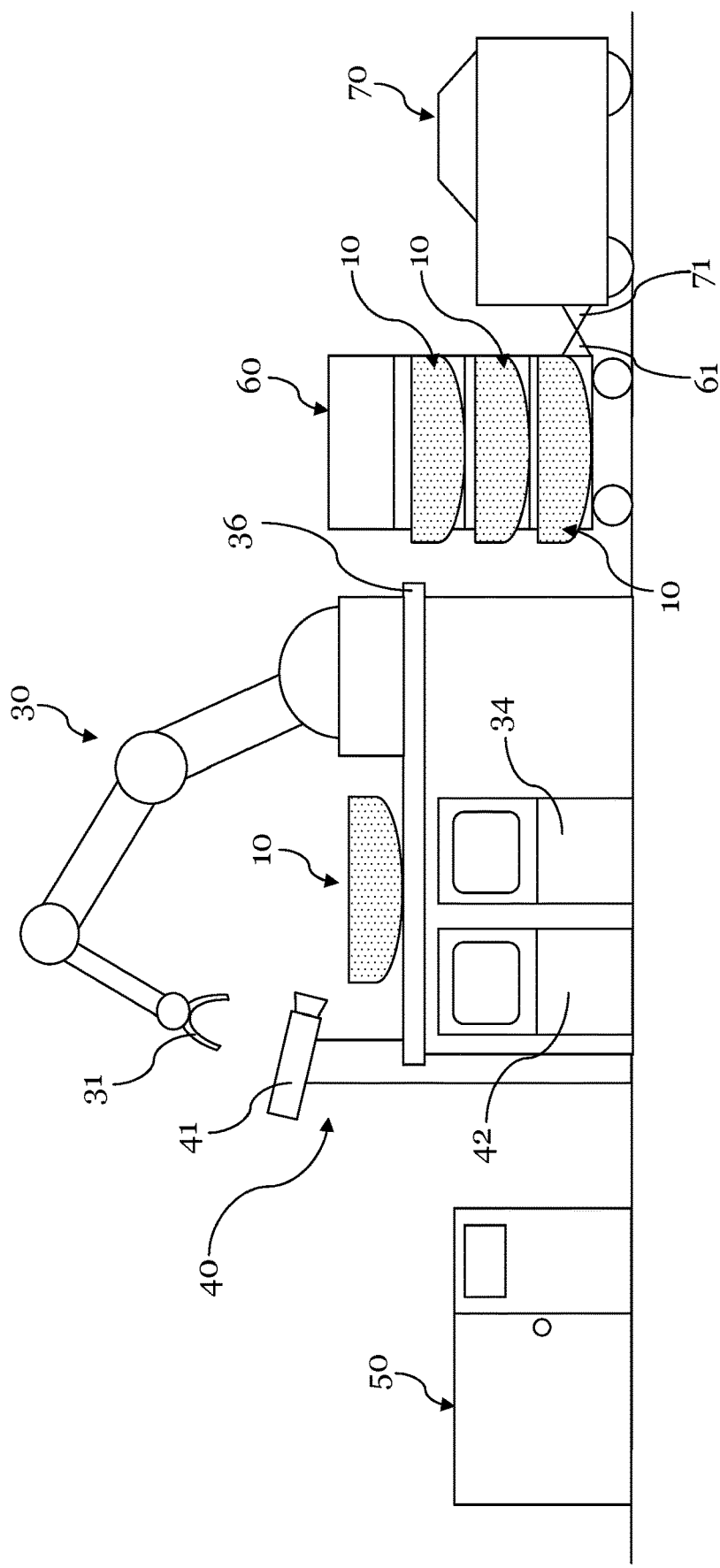

INSTRUMENT TRAY FOR SURGICAL INSTRUMENTS

CROSS-REFERENCE TO RELATED APPLICATIONS

This application is a national phase application under 35 U.S.C. § 371 of International Patent Application No. PCT/EP2018/064128, filed May 30, 2018 (pending), which claims the benefit of priority to German Patent Application No. DE 10 2017 209 966.6, filed Jun. 13, 2017, the disclosures of which are incorporated by reference herein in their entirety.

TECHNICAL FIELD

The present invention relates to an instrument tray for storing and providing surgical instruments, and to a system and a method for handling such trays, at least partially automatically.

BACKGROUND

Surgical instruments (also referred to as surgical equipment or surgical tools), as are typically used in operating theaters in hospitals, are primarily reused and must therefore move back and forth between the operating theater and sterilization department in a circulation process. In this circuit, the instruments are manually handled several times and repeatedly restored in various containers. Until now, it was virtually impossible to automize these processes, since the instruments were typically placed in instrument trays or baskets at random after having been used in the operating theater. Handling these instrument trays and the instruments they contain is therefore very laborious and accordingly expensive.

By way of example, instruments are typically circulated in a hospital as follows: In the operating theater, the surgical instruments used are non-systematically collected in instrument trays (such as wire baskets or other containers comprising openings that allow the instruments they contain to be washed). Consumables and disposable materials are thrown away. The used instruments are then transported to the sterilization department. In the sterilization department, the instrument trays are unpacked and pre-inspected by hand. In this case, individual instruments are already pre-cleaned, for example by means of ultrasound. The trays are then manually collected for the cleaning and disinfecting appliances and the instruments are then washed. The instruments that are washed and thereby cleaned are placed in a store, where they are stored until just before their next use. The instruments required for an operation are requested individually. The requested instruments are fetched from the store and transported to packing tables, where the instrument trays are manually packed or loaded for the respective operations. This working step is very complex and requires a great deal of personnel. After a visual post-inspection, the trays packed in this way are wrapped in a sterile cloth and transported to an autoclave, for example. Here they are sterilized and unloaded after the sterilization process, and transported to the operating area. If necessary, the surgical case carts are prepared with the prepared and sterilized instrument trays and taken into the operating theater. Here, the case carts are unpacked, and the sterilized instruments are spread out on the instrument tables near to the operating table so that the instruments are close at hand.

SUMMARY

The aim of the invention is to reduce the effort involved in circulating the surgical equipment or surgical instruments and therefore to reduce the costs and duration of an instrument cycle. In particular, handling of the instrument trays is intended to be simplified and preferably at least partially automated. This and other problems are solved, at least in part, by an instrument tray, a system, and a method in accordance with the present disclosure.

The invention relates to an instrument tray for storing and providing surgical instruments, comprising a container for receiving surgical instruments, the container being provided with unique visual markers for individual instruments. Unique instrument positions in the container can therefore be assigned to instruments. Here, an instrument tray is understood to mean any type of device that is suitable for receiving surgical instruments and comprises corresponding outlet openings that allow the instrument tray and the instruments it contains to be washed. For example, the instrument tray can comprise a wire basket made of metal, in which the instruments are placed, and which can be inserted into a correspondingly suitable washing device together with the instruments. The cleaning and disinfecting agents can therefore easily drain away so that the instrument tray, together with the cleaned instruments, can be removed from the washing device in one piece. The container for receiving the instruments comprises a unique position for each individual instrument, which is defined by the marker. The instruments are therefore not loosely and randomly received in the container, but each instrument has its own, uniquely assigned place in the container. Amongst other things, this is advantageous in that the instruments can be completely provided in this form in the container in the operating theater, for example, and not be manually removed from the container and provided on the operating table for a prolonged amount of time before the operation. All the instruments lie in fixedly defined and marked points such that manual arrangement of the instruments on the instrument tables that are near to the operating table is no longer necessary. It is particularly advantageous for these instruments trays as a whole to be sterilizable, i.e. together with the complete set of instruments. The loaded and sterilized instrument trays then remain in this state and do not need to be repacked again. In addition, it is advantageous in principle for the instrument trays to be of approximately the same size as the instrument tables. The instruments can therefore be provided on the instrument tables in the operating theater without the instruments needing to be removed from the tray by hand. Instead, during the operation, the operating surgeon or an assistant can remove the instruments directly from the tray as needed. Furthermore, the markers are advantageously detachably fastened such that the instrument positions, and, if necessary, the type of instruments, can be adapted freely and individually.

The visual markers are preferably silhouettes of the individual instruments. In this case, these are particularly preferably the same size as the instruments they represent or depict. Each silhouette is located at the exact point at which the particular instrument is intended to be positioned. In this way, empty places are immediately visible and incorrect insertions can be immediately and readily detected. The use of unique visual markers, such as said silhouettes, makes it possible in particular for the inventive instrument trays to be handled automatically. On account of the markers, it is in particular possible, for example using computer-aided image processing, to simply and reliably determine the loaded state of an instrument tray. Instrument trays of the prior art do not make this possible, since here a plurality of instruments is randomly arranged on top of one another. The use of silhouettes of the individual instruments as markers makes it easier to reliably automatically record and process images of the instrument trays. The silhouettes are also an especially valuable aid for manual visual checks or manual post-loading, if required, which can increase the quality and efficiency of the circulation of the instruments.

The container preferably comprises retaining clips, which are designed to releasably hold the instruments with a degree of clearance. The instruments should in particular not be held too tightly, since they may need to be easily and quickly removed during an operation. Holding the instruments with a degree of clearance is also advantageous in that the instruments can be completely wetted with the cleaning liquids during a cleaning process.

The retaining clips are particularly preferably provided with fastening pins, and the container comprises openings through which the pins can be guided. In this case, the pins are deformable in order to fix the retaining clips to the container. Such retaining clips make it possible to load the instrument tray individually, in which said tray, together with the visual markers, can be freely positioned and fixed to the container. For this purpose, the pins are guided through corresponding openings in the container, such as openings in a mesh basket when the container is formed as a mesh basket, and the pins are then bent on the bottom of the container, fixing the retaining clips to the container. This can optionally be done in the hospital itself, since the pins can be bent using a simple pair of pliers, if necessary.

Each of the retaining clips preferably comprises two spring arms, which are designed to receive part of an instrument so as to releasably hold it therebetween with a degree of clearance. In this case, the springs are arranged with respect to one another so as to form a snap-fit connection with the instruments to be held. Simple loading of the container with instruments is therefore possible and still guarantees the simple and convenient removal of the instruments from the container, for example during an operation.

The instrument tray is generally preferably autoclavable. All the materials of the instrument tray are therefore preferably selected such that the instrument tray can be directly inserted into an autoclave and sterilized therein, without additional modifications. The instrument tray is preferably made of metal.

More preferably, the instrument tray comprises coupling devices, which are designed to arrange the instrument tray in a surgical case cart. This ensures safe transport of the instrument trays.

The instrument positions are generally preferably arranged in one plane in the container such that the instruments do not overlap or do not substantially overlap inside the container. This is the difference with respect to the prior art, in which the instruments are provided tightly packed or bundled or stacked in small baskets before an operation, or (for example after the operation) are arranged in the baskets at random or thrown into the baskets at random. By being arranged in one plane, i.e. next to one another, it is now possible for the instruments to be handled automatically, for example by means of a suitable manipulator. In addition, the arrangement in one plane allows for the direct use of the loaded instrument tray in the operating theater. It is no longer necessary to remove the instruments from the tray and provide them, since the instrument tray itself already offers suitable provision thereof. This considerably decreases the operation preparation time.

The present invention also relates to a system, comprising an instrument tray as described above, and a manipulator, which manipulator is designed for loading this instrument tray with surgical instruments and/or for removing instruments from the instrument tray. As explained above, the inventive instrument tray allows the tray to be loaded or handled automatically. Since each instrument has a unique instrument position in the tray, the inventive trays make it possible to handle the instruments they contain by means of a manipulator, for example partially or fully automatically.

Manipulators, and in particular robots, are programmable machines that are designed in particular for automatically handling or processing objects or workpieces. A typical example of such manipulators are jointed-arm robots, which comprise a plurality of links which are in turn interconnected by means of corresponding joints. A receptacle for a tool is typically provided at a free end.

The system preferably also comprises an image-detecting unit, which has a camera for recording images and an image-processing apparatus, the image-detecting unit transmitting information relating to the loaded state of the instrument tray to the control apparatus of the manipulator. The control apparatus is designed to control the manipulator using the information in order to insert instruments into and/or remove instruments from the instrument tray. The system therefore makes it possible to automatically record the loaded state and to automatically control the manipulator to detect incorrectly positioned instruments, for example, and to automatically correctly arrange them in order to replace missing instruments or to targetedly remove specific instruments from the instrument tray.

The system preferably also comprises a surgical case cart, which is suitable for receiving instrument trays, and a driverless transport vehicle (also called an automated guided vehicle, AGV) for moving the case cart. Driverless transport vehicles are floor-bound conveying means comprising their own travel drive, which are automatically controlled and contactlessly guided. The use of conveying means of this type can further simplify the automation of the handling of the instrument trays.

The system preferably also comprises a sterilization device, the control apparatus of the manipulator being designed to grip the instrument tray when a full or substantially full loaded state is detected, and to move the tray into the sterilization device and remove it again when the sterilization process has finished. The detection of the loaded state is simplified by the special features of the inventive instrument tray, and therefore the tray can be reliably detected and handled by a manipulator.

It is generally advantageous for the instrument tray to be provided with unique machine-readable codes. This makes it possible to uniquely identify different trays, making automatic handling easier.

The invention also relates to a method for at least partially automatically handling an instrument tray as described here, said method comprising the following steps: providing an inventive instrument tray; providing a manipulator having an associated image-detecting unit, which comprises a camera for recording images and an image-processing apparatus; recording an image of the instrument tray and detecting the loaded state by means of the image-detecting unit; and controlling the manipulator, taking into consideration the loaded state, in order to insert instruments into and/or remove instruments from the instrument tray.

On account of the preset instrument positions in the inventive instrument tray, automation is made possible by means of manipulators and with the aid of image processing.

For example, instrument trays that having missing parts can now be automatically detected by means of image processing and completed or corrected, if necessary. The precisely preset instrument positions advantageously make it possible for the instrument trays to be loaded by means of a robot. In this case, the integration of robots assists with the reliability of the sterilization process, since robots can be operated in a sterile manner. The image-processing apparatus can be a computer that is specially designed for this, for example, or can be integrated in the manipulator controller, or can share hardware components therewith.

In the present method, the manipulator is preferably therefore controlled such that the manipulator fills empty instrument positions. In this case, not all of the empty positions have to be filled, but it is likewise conceivable for the manipulator to only fill specific preset positions.

In the method, the manipulator is more preferably controlled such that the manipulator removes selected instruments when instructed by a user. This can be done during an operation, for example, if a robot passes the instruments to the surgeon.

Even more preferably, when a full or substantially full loaded state is detected, the following steps are carried out: grasping the instrument tray by means of the manipulator; moving the instrument tray into a sterilization device by means of the manipulator; carrying out a sterilization process in the sterilization device; and then removing the sterilized instrument tray from the sterilization device by means of the manipulator. In the present method, image processing makes it possible for the system to automatically detect whether or not an instrument tray is fully loaded or is loaded in accordance with specific requirements, for example, and the manipulator can automatically supply the tray to a sterilization device in this case. Since the sterilized tray does not have to be manually handled by a person, but can be removed by the manipulator, the tray remains sterile.

Once the sterilized instrument tray has been removed by means of the manipulator, the following steps are preferably also carried out: arranging the instrument tray in a surgical case cart by means of the manipulator; and moving the case cart to an operating theater by means of a driverless transport vehicle. The instrument tray is advantageously designed such that it can be arranged in a surgical case cart. For automatic handling, a machine-readable code (for example a barcode, QR code, slotted grating, etc.) is preferably also provided in suitable positions on each instrument tray. The code also advantageously allows the tray to be uniquely identified, for which purpose corresponding information can be stored in a database, for example. The case cart advantageously comprises a corresponding drawbar for attachment to the transport vehicle so that the driverless transport vehicle can couple to the case cart and move it. For this purpose, the case cart can comprise machine-readable markings, for example, such that a transport vehicle equipped with image detection can automatically detect which case cart is intended to be moved.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

FIG. 3 is a schematic view of a system for automatically handling instrument trays.

DETAILED DESCRIPTION

Figure 1:
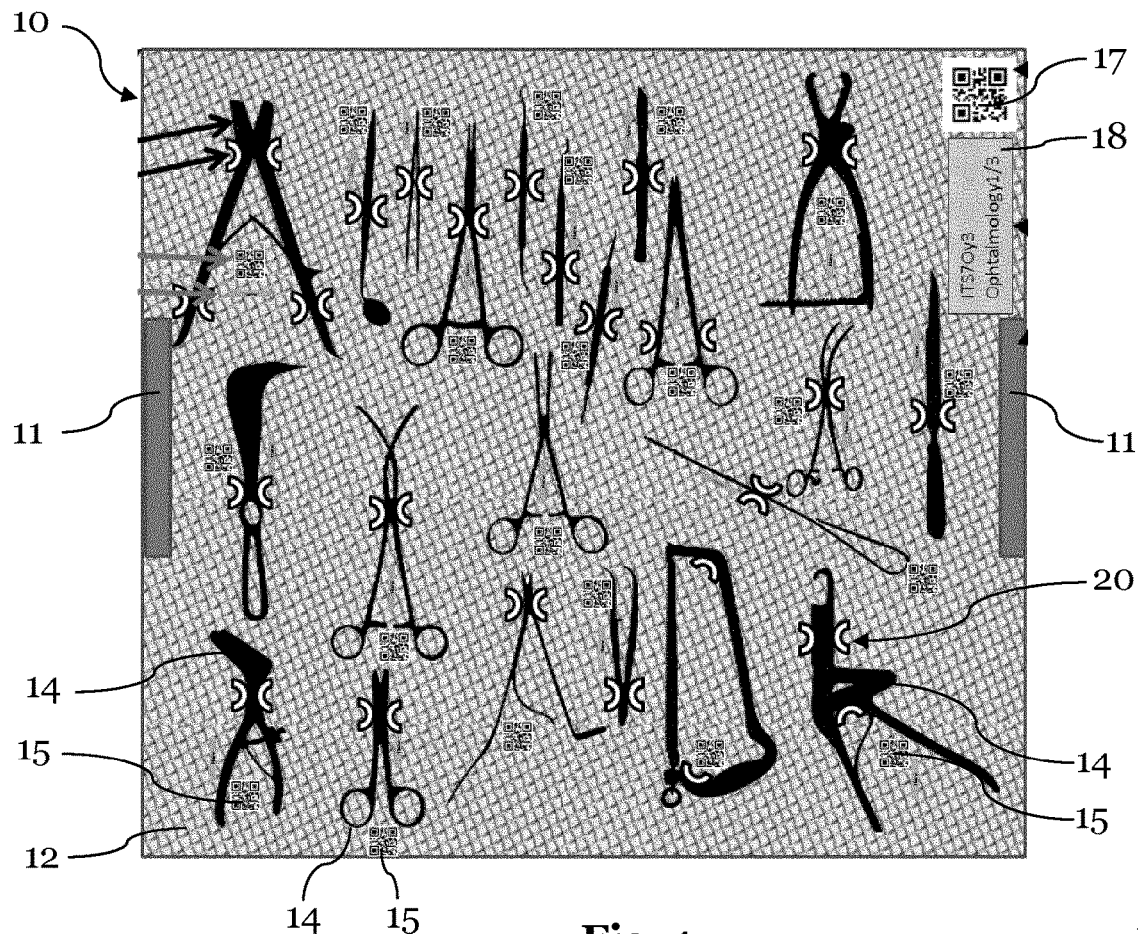
FIG. 1 is a schematic plan view of an instrument tray.

FIG. 1 shows an instrument tray 10 for storing and providing surgical instruments. The system comprises a container 12 for receiving the instruments, which is in the form of a wire basket. The container 12 does not have to comprise a basket or a mesh, instead all that matters is that the bottom of the container is perforated such that cleaning liquid or sterilization liquid can drain away, if necessary. The bottom of the container 12 is provided with a series of unique visual markers 14. In the embodiment shown, the markers 14 are silhouettes of the individual instruments that are to be fastened in the position indicated. The markers or silhouettes 14 have the same shape and size as the instruments they represent. The surgical instruments shown schematically in FIG. 1 are therefore not intended to represent the instruments themselves, but merely silhouettes of the instruments. An individual machine-readable code 15 is also assigned to each silhouette or each marker 14, by means of which the associated instrument can likewise be uniquely identified. The instrument tray 10 also comprises a machine-readable code 17, by means of which the tray can be uniquely identified. In addition to the code 17, an alphanumerical designation 18 is provided for the tray. Reference signs 11 denote coupling devices, by means of which the tray can be arranged in a surgical case cart, for example. The coupling devices 11 can also serve as handles for a manipulator or a human user. All the instrument positions in the container 12 are advantageously arranged in one plane such that the instruments do not overlap in the container. One or more retaining clips 20 is/are assigned to each instrument position, which is specified by a market or a silhouette 14, by means of which clips the respective instruments can be releasably held with a degree of clearance.

Figure 2A:
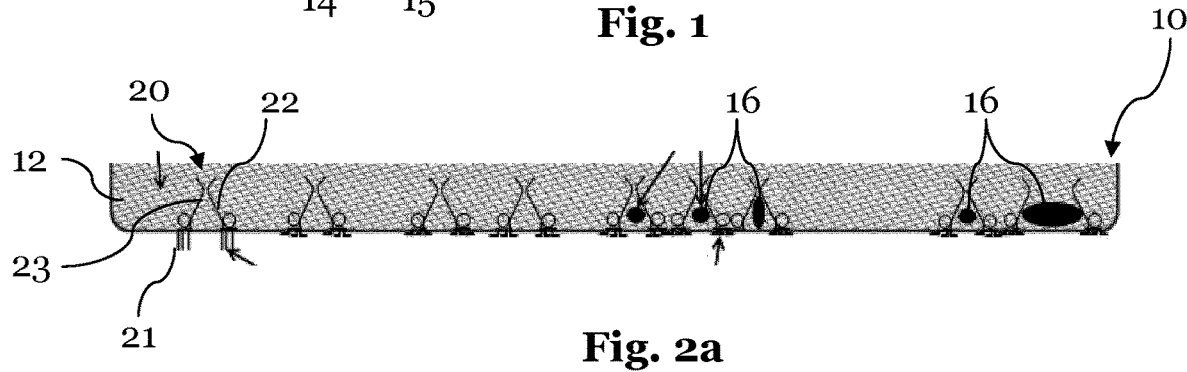
FIG. 2a is a schematic sectional side view of the instrument tray in FIG. 1.
Figure 2B:
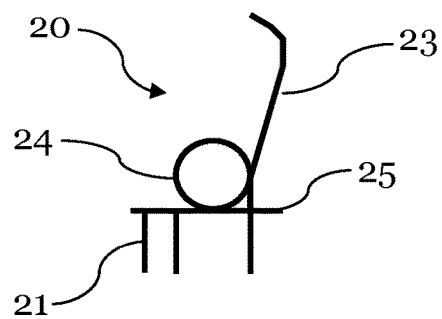
FIG. 2b is a schematic detailed view of a retaining clip.

FIG. 2a shows the tray from FIG. 1 is a schematic sectional side view. Reference signs 16 denote different surgical instruments (only schematic cross sections of which can be seen in the figure), which are held by the retaining clips 20. In the embodiment shown (see also FIG. 2b), each retaining clip comprises two spring arms 22, 23, which are resiliently provided on a base 25 by means of springs 24. The base 25 is provided with one or more fastening pins 21, which can be inserted through the openings in the bottom of the container 12 such that the fastening pins 21 extend out of the lower side of the container 12. This is shown in the left-hand fastening clip in FIG. 2b. The fastening pins 21 are deformable and can bend in order to fix the retaining clips to the bottom of the container 12. This is shown in the rest of the fastening clips in FIG. 2b. In this way, the retaining clips can be individually configured and fixed in the container 12 as necessary.

FIG. 3 is a schematic view of a system for partially or fully automatically handling instrument trays 10. The system comprises a manipulator 30, which is provided in the form of a jointed-arm robot. The manipulator 30 supports a gripper 31, which can grasp surgical instruments. An instrument tray 10 is provided on a table 36. An image-detecting unit 40 comprising a camera 41 for recording images and an image-processing apparatus 42 is arranged such that it can record images of the inside the instrument tray. In this case, the image-detecting unit 40 is designed to transmit information relating to the loaded state of the instrument tray 10, for example, to a control apparatus 34 of the manipulator 30. The control apparatus 34 of the manipulator 30 can then in turn accordingly control the manipulator 30 in order to remove instruments from, or add them to, the tray 10, taking into account the information relating to the loaded state, for example. The system shown also comprises a surgical case cart 60, in which additional instrument trays 10 are arranged. The case cart 60 is coupled to a driverless transport vehicle 70 by means of drawbars 61 and 71. The driverless transport vehicle 70 can therefore autonomously move the case cart 60, for example from a store to an operating theater. Furthermore, a sterilization device 50 is provided, such as an autoclave, and the control apparatus 34 of the manipulator 30 is designed to move instrument trays 10, for example, into the sterilization device 50 and to remove them therefrom again. The image-detecting unit 40 can, for example, detect which instruments have to be arranged in which positions, for example by means of the silhouettes 14. Alternatively or in addition, the image-detecting unit 40 can also record and correspondingly process the various machine-readable codes 15 and 17.

The case cart 60 preferably also comprises machine-readable codes such that transport vehicles 70 equipped with corresponding image-detecting devices can identify the case cart 60, for example. For example, the central sterilization department building of a hospital can comprise a store of fully loaded and sterile instrument trays, which can be coupled, when necessary. The store can be operated by a store robot and the transport vehicles 70 can automatically fetch the required case carts for specific operations.

In a preferred embodiment, the instruments trays are provided in different configurations comprising different surgical instruments. For example, instrument trays that have a basic configuration and are required for virtually every operation can be provided, whereas additional special instrument trays only contain specific instruments that are used depending on the operation.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

LIST OF REFERENCE NUMERALS 10 instrument tray
11 coupling device
12 container
14 marker (silhouette)
15 machine-readable code
16 surgical instrument
17 machine-readable code
18 alphanumerical code
20 retaining clips
21 fastening pin
22, 23 spring arms
30 manipulator
32 gripper
34 control apparatus of the manipulator
36 table
40 image-detecting unit
41 camera
42 image processing apparatus
50 sterilization device
60 surgical case cart
61 drawbar for the case cart
70 driverless transport vehicle
71 drawbar for the driverless transport vehicle

What is claimed is:

1. A system, comprising:
an instrument tray for storing and providing surgical instruments, the instrument tray comprising:
a container configured to receive surgical instruments,
at least one unique visual marker on the container, the at least one visual marker associated with an individual surgical instrument and defining a unique position in the container for locating the associated instrument,
wherein the at least one visual marker comprises a silhouette of the associated individual instrument and is approximately the same size as the associated instrument, and
a plurality of retaining clips on the container, the retaining clips configured to releasably hold the instruments on the container with a degree of clearance;
wherein:
the retaining clips comprise fastening pins,
the container further comprises a plurality of openings configured to receive the fastening pins therethrough, and
the fastening pins are deformable in order to fix the retaining clips to the container;
wherein the retaining clips each comprise two spring arms, the spring arms configured to receive part of an instrument so as to releasably hold the instrument therebetween with a degree of clearance;
wherein the instrument tray is autoclavable; and
wherein:
the at least one visual marker comprises a plurality of visual markers, and
the plurality of visual markers are arranged on the container in a single plane such that instruments received at the respectively defined instrument positions do not overlap inside the container;
a robotic manipulator configured for at least one of loading the instrument tray with surgical instruments or removing surgical instruments from the instrument tray;
an image-detecting unit including a camera for recording images and an image- processing apparatus;
the image-detecting unit configured to transmit information related to a loaded state of the instrument tray to a control apparatus of the manipulator;
the control apparatus configured to control the robotic manipulator using the information to at least one of insert instruments into the instrument tray or remove instruments from the instrument tray;
a surgical case cart configured to receive instrument trays; and
a driverless transport vehicle (AGV) for moving the case cart; and
a sterilization device;

wherein the control apparatus of the manipulator is configured to control the robotic manipulator to:
grip an instrument tray in response to the image-detecting unit detecting a fully loaded or a substantially fully loaded state of the instrument tray,
move the instrument tray into the sterilization device for sterilizing instruments carried on the instrument tray, and
remove the instrument tray from the sterilization device when a sterilization process has finished.

2. A method for at least partial automatic handling of an instrument tray, the method comprising:
recording an image of the instrument tray with an image-detecting unit, wherein the instrument tray is autoclavable and comprises:
a container configured to receive surgical instruments,
a plurality of unique visual markers on the container, each visual marker associated with an individual surgical instrument and defining a unique position in the container for locating the associated instrument,
wherein each visual marker comprises a silhouette of the associated individual instrument and is approximately the same size as the associated instrument,
the plurality of visual markers arranged on the container in a single plane such that instruments received at the respectively defined instrument positions do not overlap inside the container,
a plurality of retaining clips on the container, the retaining clips comprising fastening pins configured to releasably hold the instruments on the container with a degree of clearance,
a plurality of openings in the container and configured to receive the fastening pins therethrough,
wherein the fastening pins are deformable in order to fix the retaining clips to the container, and
wherein the retaining clips each comprise two spring arms, the spring arms configured to receive part of an instrument so as to releasably hold the instrument therebetween with a degree of clearance;
determining from the recorded image a loading state of the instrument tray using the image-detecting unit;
controlling a robotic manipulator to at least one of insert instruments into the instrument tray or remove instruments from the instrument tray based on the determined loading state of the instrument tray;
in response to the image-detecting unit detecting a fully loaded or a substantially fully loaded state of an instrument tray, then:
controlling the robotic manipulator to grasp the instrument tray,
controlling the robotic manipulator to move the instrument tray into a sterilization device,
sterilizing the instruments and instrument tray in the sterilization device, and
controlling the robotic manipulator to remove the sterilized instrument tray from the sterilization device;
controlling the robotic manipulator to arrange the sterilized instrument tray in a surgical case cart; and
moving the surgical case cart to an operating theater using a driverless transport device (AGV).

3. The method of claim 2, further comprising:
controlling the robotic manipulator to fill empty instrument positions of the instrument tray with respective surgical instruments.

4. The method of claim 2, further comprising:
controlling the manipulator to remove selected instruments from the instrument tray when commanded by a user.

* * * * *